United States Patent [19]
Wade et al.

[11] 3,935,227
[45] Jan. 27, 1976

[54] 2-[(SUBSTITUTED-PIPERIDINYL OR TETRAHYDROPYRIDINYL)ALKYL]-1H-BENZ[DE]ISOQUINOLINE-1,3(2H)-DIONES

[75] Inventors: Peter C. Wade, Pennington, N.J.; Berthold Richard Vogt, Yardley, Pa.

[73] Assignee: E. R. Squibb & Sons, Inc., Princeton, N.J.

[22] Filed: Aug. 28, 1974

[21] Appl. No.: 501,411

[52] U.S. Cl. ... 260/281 S; 260/281 N; 260/281 NH; 260/293.78; 260/293.72; 260/293.84; 424/258
[51] Int. Cl.² .................................. C07D 401/06
[58] Field of Search ....... 260/281 N, 281 NH, 281 S

[56] References Cited
UNITED STATES PATENTS

| | | | |
|---|---|---|---|
| 3,247,208 | 4/1966 | Schenker | 260/281 N |
| 3,330,834 | 7/1967 | Senshu | 260/281 |
| 3,697,525 | 10/1972 | Okada | 260/281 N |

FOREIGN PATENTS OR APPLICATIONS

| | | | |
|---|---|---|---|
| 39-27127 | 11/1964 | Japan | 260/281 N |

OTHER PUBLICATIONS
Organic RXNS (1973) 20, 456–459; 464–467, (1973).
Petrenko et al., Chem. Abs. 69, 76990t (1968).
Morgan et al., Chem. Abs. 25, 39884, (1931).
Kaufler et al., Chem. Berrchte 40, 2363, (1907).
Lewkchardt, J. Pr. Chem. 1890, ii, 41, 170.
Nursten et al., Chem. Abs. 44, 7820–7821, (1950).
Physicians Desk Reference, pp. 951, 1477, (1974).
Merck Index, 8th Edition, p. 735.
Webb et al., Chem. Abs. 76, 59284t (1972).
Vernon et al., Chem. Abs. 64, 2029e (1966).
Wills et al., Chem. Abs. 75, 87712d (1971).
Daewonski et al., Chem. Abs. 21, 2682–2683, (1927).

Primary Examiner—Donald G. Daus
Assistant Examiner—Mark L. Berch
Attorney, Agent, or Firm—Lawrence S. Levinson; Merle J. Smith; Stephen B. Davis

[57] ABSTRACT

Compounds of the following formula and their acid addition salts

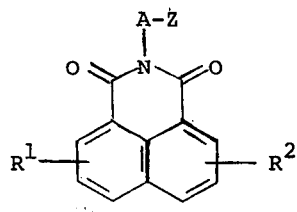

wherein $R^1$ and $R^2$ are independently selected from hydrogen, halogen, lower alkyl, lower alkoxy, lower alkylthio, nitro, cyano, amino and trifluoromethyl; A is a straight or branched chain alkylene of 1 to 8 carbons; and Z is selected from

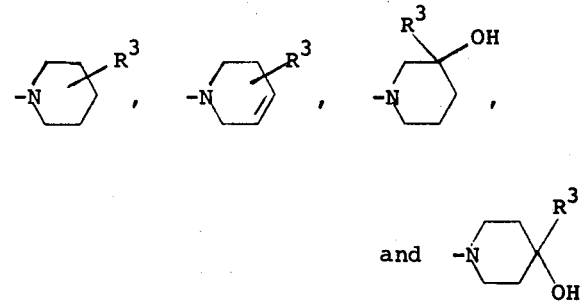

wherein $R^3$ is selected from phenyl, phenyl-lower alkyl, and substituted phenyl and phenyl-lower alkyl are disclosed. These compounds exhibit antidepressant and anti-anxiety activity. In addition these compounds are useful as anti-inflammatory agents.

25 Claims, No Drawings

2-[(SUBSTITUTED-PIPERIDINYL OR TETRAHYDROPYRIDINYL)ALKYL]-1H-BENZ-[DE]ISOQUINOLINE-1,3(2H)-DIONES

BACKGROUND OF THE INVENTION

Various naphthalimide compounds have been developed for use as dyes and optical brightening agents. Kimura et al., for example, at Chem. Abst., Vol. 62, 11950c, disclose N-[2-piperidinoethyl]-4-methoxy-1,8-naphthalimide (i.e. 6-methoxy-2-[2-(1-piperidinyl)ethyl]-1H-benz[de]isoquinoline-1,3(2H)-dione under the current Chem. Abst. nomenclature) as an optical brightening agent. Noguchi et al. in U.S. Pat. No. 3,625,947 disclose 2-[2-(2 or 4-pyridyl)ethyl]-1H-benz[de]isoquinoline-1,3(2H)-diones as fluorescent whitening agents.

Schenker et al. in U.S. Pat. No. 3,247,208 disclose that 1H-benz[de]isoquinoline-1,3(2H)-diones having a (1-substituted-4-piperidinyl) group in the 2-position possess anesthetic properties. Carron et al. in French Pat. No. 2,167,355 disclose that (4-phenyl)piperidine-2,6-diones having an alkylheteroalkyl substituent at the 1-position possess antidepressant activity. Imides having a nitroimidazolyethyl group as an N-substituent and possessing anti-bacterial and anti-protozoal activity are disclosed in U.S. Pat. Nos. 3,642,836 and 3,770,763 to Cusic et al. Certain imido dicarboxylic acid imides possessing various pharmacological properties are disclosed in U.S. Pat. No. 3,560,495 to Frankus et al.

SUMMARY OF THE INVENTION

This invention relates to new 2-[(substituted-piperidinyl or tetrahydropyridinyl)alkyl]-1H-benz-[de]isoquinoline-1,3(2H)-diones and their acid addition salts of the formula (I)

The symbols have the following meaning in formula I and throughout this specification.

$R^1$ and $R^2$ are each independently selected from hydrogen, halogen (preferably Br, Cl, or F), $CF_3$, lower alkyl, lower alkoxy, lower alkylthio, nitro, amino and cyano.

A is straight or branched chain alkylene of 1 to 8 carbons.

Z is selected from wherein
$R^3$ is selected from phenyl, phenyl-lower alkyl, and substituted phenyl and phenyl-lower alkyl.

DETAILED DESCRIPTION OF THE INVENTION

The various groups represented by the symbols have the meanings defined below and these definitions are retained throughout this specification.

The lower alkyl groups referred to throughout this specification include straight or branched chain hydrocarbon groups containing 1 to 4 carbons. Examples of the type of groups contemplated are methyl, ethyl, propyl, isopropyl, butyl, etc. The lower alkoxy groups include such lower alkyl groups attached to an oxygen, e.g., methoxy, ethoxy, propoxy, etc. The phenyl-lower alkyl groups include such lower alkyl groups attached to a phenyl, e.g., benzyl, phenethyl, etc. The lower alkylthio group include such lower alkyl groups attached to a sulfur, e.g., methylthio, ethylthio, etc.

Straight or branched chain alkylene of 1 to 8 carbons is intended to include group such as $-(CH_2)_n-$ wherein n is 1 to 8, $$-CH_2-\underset{CH_3}{CH}-, \quad -CH_2-\underset{C_2H_5}{CH}-(CH_2)_2-, \quad -CH_2-\underset{CH_3}{CH}-\underset{CH_3}{CH}-CH_2-, \text{ etc.}$$

The substituted phenyl and phenyl-lower alkyl groups include one or more substituents such as lower alkyl, lower alkoxy, halogen (preferably F, Cl, or Br), $CF_3$, amino, nitro and the like. Examples of the type of groups contemplated are o-, m- or p-chlorophenyl, o-, m-, or p-tolyl, 2,5-dibromophenyl, 3,5-dimethylphenyl, o-, m-, or p-methoxyphenyl, o-, m-, or p-chlorobenzyl, o-, m-, or p-methoxybenzyl, o-, m-, or p-bromophenethyl, etc.

Preferred embodiments of this invention are as follows:

At least one of $R^1$ or $R^2$ is hydrogen and the other is hydrogen, Cl, F, Br, $CH_3$ or $OCH_3$.

A is straight or branched chain alkylene of 1 to 6 carbon atoms.

The most preferred compounds are:

$R^1$ and $R^2$ are both hydrogen.

A is $-(CH_2)_n-$ wherein n is an integer from 2 to 6, especially $-(CH_2)_4-$.

The $R^3$ substituent or $R^3$ and OH substituents are located at the 4-position of the piperidinyl or tetrahydropyridinyl radical.

The new compounds of this invention are prepared by the following reactions where A is straight or branched chain alkylene of 2 to 8 carbons.

The substituted naphthalic anhydride of formula II (II)

is reacted with an alkanolamine of formula III (III)
H₂N—A—OH
to yield the alcohol of formula IV mula I by reacting the anhydride with compounds of formula VI.
(VI)
H₂N—A—Z The following schematic summarizes the reactions described above.

where A is straight or branched chain alkylene of 2 to 8 carbons

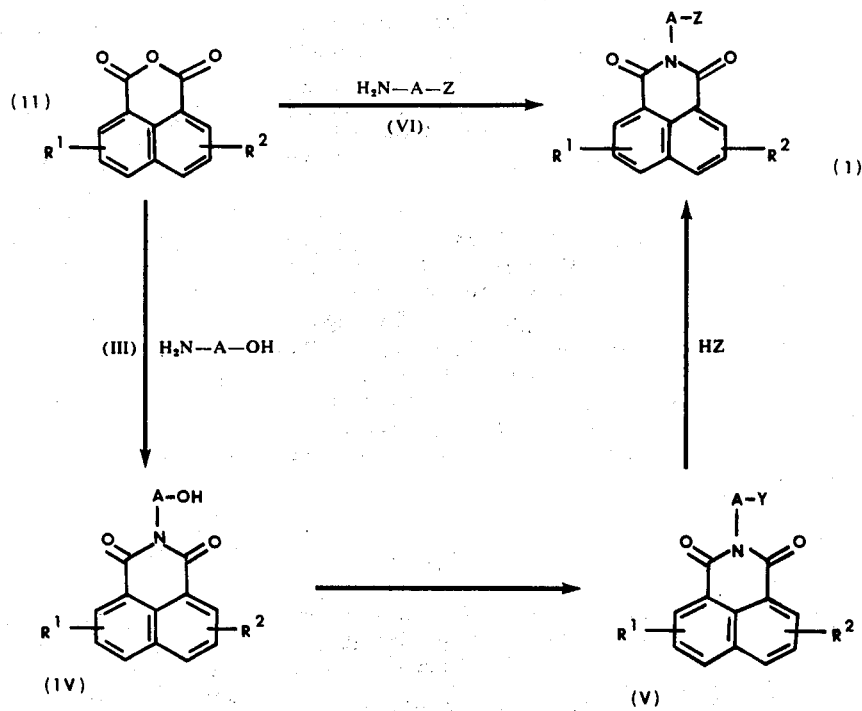

(IV)

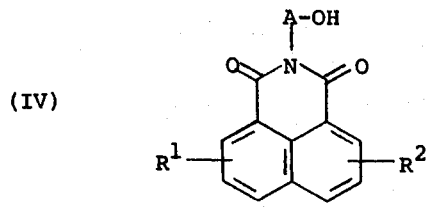

The alcohol of formula IV is converted to the intermediate of formula V (V)

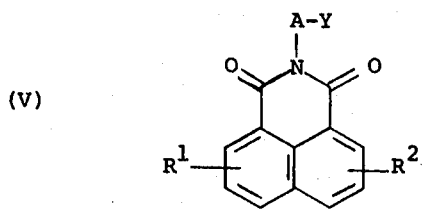

where Y is a leaving group such as tosylate, methane sulfonate or halogen by treating the alcohol with p-toluenesulfonyl chloride, methane sulfonyl chloride, thionyl chloride, thionyl bromide or hydrogen iodide.

The intermediate of formula V is then converted to the final products of formula I by reactions with compounds of the formula HZ.

The substituted naphthalic anhydride of formula II can be converted directly to the final products of for- Also, the intermediate of formula V can be prepared by combining a substituted naphthalimide of formula VII (VII)

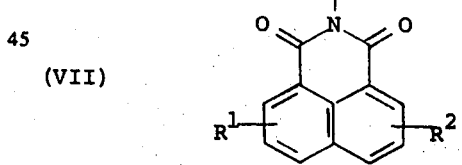

in an organic solvent with a polar organic solvent solution of a base, as for example an alcohol solution of potassium hydroxide, followed by the addition of a solution of the compound of formula VIII,
(VIII)
Y'—A—Y
wherein Y' and Y are the same or different and are leaving groups selected from tosylate, methane sulfonate, or halogen and A is a straight or branched chain alkylene of 2 to 8 carbons.

Alternatively, the compounds of formula I wherein A is straight or branched alkylene of 2 to 8 carbons can be prepared by combining the anion of the substituted naphthalimide of formula VII, described above, with a solution of the compound of formula IX,
(IX)
Y—A—Z
wherein Y is a leaving group as previously defined.

Compounds of formula I where A is —CH$_2$— are prepared by reacting the substituted naphthalimide of formula VII suspended in a polar organic solvent such as dimethylformamide (DMF) with compounds of the formula HZ and a source of formaldehyde such as aqueous formaldehyde or paraformaldehyde.

The various starting materials such as the substituted anhydrides of formula II and the alcohols of formula IV and the substituted naphthalimides of formula VII are known in the art or are readily obtainable by known procedures. Further process details are also provided in the illustrative examples.

The compounds of formula I wherein either or both R$^1$ and R$^2$ are amine or R$^3$ is an amino substituted phenyl or phenyl-lower alkyl are prepared by reducing the corresponding nitro substituted compound with a reducing agent such as hydrogen over a palladium catalyst or a suitable chemical reducing agent. This is preferably done as the last stage in the reaction procedures described above.

Depending on the reaction conditions and the starting materials used, the new compounds are obtained in the free form or in the form of their acid addition salts. The salts thereof can be converted into the free compounds in a known manner such as by reaction with a basic agent. Free bases which may be obtained can be converted into pharmaceutically acceptable acid addition salts by reaction with a variety of acids. Acids useful for preparing these acid-addition salts include, inter alia, inorganic acids, such as the hydrohalic acids (e.g. hydrochloric and hydrobromic acid), sulfuric acid, nitric acid, and phosphoric acid, and organic acids such as maleic, fumaric, tartaric, citric, acetic, benzoic, 2-acetoxybenzoic, salicyclic, succinic, nicotinic, methanesulfonic or cyclohexanesulfamic.

The new compounds of the present invention including the acid addition salts are capable of modifying the central nervous system. When administered to mice, cats, rats, dogs, and other mammalian species in amounts ranging from about 0.5 mg. to about 100 mg. per kg. of body weight per day, these compounds in particular exhibit anti-depressant and anti-anxiety activity. A preferred dosage regimen for optimum results would be from about 1 mg. to about 5 mg. per kg. of body weight per day, and such dosage units are employed so that a total of from about 35 mg. to about 3 g. of active ingredient in single or divided doses are administered in a 24 hour period.

Compounds of formula I when administered to rats within the above stated preferred dosage range produced a significant anti-anxiety effect as demonstrated by increases in behavior which were formerly suppressed by punishment in a conflict test procedure [cf. J. R. Vogel, B. Beer, D. Clody, Psychopharmacologist, 21, 1 (1970)].

The compounds of formula I are also useful as anti-inflammatory agents and may be used, for example, in a manner similar to phenylbutazone or indomethacin. They may be used to decrease joint swelling, tenderness, pain and stiffness in mammalian species, e.g., in conditions such as rheumatoid arthritis. The quantity administered ranges from about 1 mg. to about 15 mg. per kg. of body weight per day.

For any of these pharmaceutical purposes a compoud or mixture of compounds of formula I or their pharmaceutically acceptable acid addition salts may be administered orally or parenterally in a conventional dosage form such as tablet, capsule, injectable or the like. These may be conventionally formulated in an oral or parenteral dosage form by compounding with a conventional vehicle, excipient, binder, preservative, stabilizer, flavor or the like as called for by accepted pharmaceutical practice.

The following examples are illustrative of the invention and represent preferred embodiments. Other modifications may be readily produced by suitable variations of the reactions. All temperatures are on the centigrade scale.

EXAMPLE 1

2-[2-(4-Phenyl-1-piperidinyl)ethyl]-1H-benz-[de]isoquinoline-1,3(2H)-dione, hydrochloride (1:1)

a.

2-(2-Hydroxyethyl)-1H-benz[de]isoquinoline-1,3(2H)-dione 50 g. (0.252 mole) of naphthalic anhydride and 16 g. (0.262 mole) of ethanolamine are refluxed for three hours in 200 ml. of water (the solution is never complete). After cooling to 25° the water is decanted off and the residue recrystallized from 95% ethanol to yield 47.8 g. of 2-(2-hydroxyethyl)-1H-benz[de]isoquinoline-1,3(2H)-dione; m.p. 172°–173°.

b.

2(-2-Hydroxyethyl)-1H-benz[de]isoquinoline-1,3(2H)-dione, 4-methylbenzenesulfonate ester 52 g. (0.216 mole) of the 2-(2-hydroxyethyl)-1H-benz[de]isoquinoline-1,3(2H)-dione and 100 g. (0.525 mole) of p-toluenesulfonyl chloride are added to 600 ml. of pyridine previously cooled to 5°. The mixture is shaken briefly then allowed to stand overnight at 5°. The mixture is then poured into 3000 ml. of ice and water, stirred for 15 minutes and filtered. The insoluble material is stirred with fresh water, filtered off again and dried overnight at 25° (0.1 mm.) yielding 83 g. of 2-(2-hydroxyethyl)-1H-benz[de]isoquinoline-1,3(2H)-dione, 4-methylbenzenesulfonate ester.

c.

2-[2-(4-Phenyl-1-piperidinyl)ethyl]-1H-benz-[de]isoquinoline-1,3(2H)-dione, hydrochloride (1:1)

10 g. (0.025 mole) of the ester, from part (b), and 8.2 g. (0.051 mole) of 4-phenylpiperidine are refluxed in 300 ml. of toluene for 1 hour. The mixture is then cooled to 25° for 3 hours and the resulting precipitate filtered off. The filtrate is shaken with excess 10% HCl (aqueous) producing a gum that is insoluble in both layers. After several minutes the gum crystallizes and is filtered from the two liquid phases. Recrystallization of the filter cake from 50% aq. ethanol and drying at 25° (200 mm.) for three days produces 8.8 g. of 2-[2-(4-phenyl-1-piperidinyl)ethyl]-1H-benz[de]isoquinoline-1,3-(2H)-dione, hydrochloride (1:1); m.p. 272°–274°.

EXAMPLE 2

2-[2-(3,6-Dihydro-4-phenyl-1(2H)-pyridinyl)ethyl]-1H-benz[de]isoquinoline-1,3(2H)-dione, hydrochloride (1:1)

10 g. (0.025 mole) of the ester from Example 1(b) and 8.1 g. (0.051 mole) of 4-phenyl-1,2,3,6-tetrahydropyridine (freed from the hydrochloride salt with aqueous NaOH, extracted into toluene and dried over 4A° molecular sieves) are refluxed in 300 ml. of toluene for 1 hour. The mixture is then cooled to 25° for 3 hours and the resulting precipitate filtered off. The filtrate is shaken with excess 10% HCl (aqueous) producing a gum that is insoluble in both layers. After several minutes the gum crystallizes and is filtered from the two liquid phases. Recrystallization of the filter cake from 600 ml. of 95% ethanol and drying at 80° (0.1 mm.) for 2 hours produces 3.5 g. of 2-[2-(3,6-dihydro-4-phenyl-1(2H)-pyridinyl)ethyl]-1H-benz-[de]isoquinoline-1,3(2H)-dione, hydrochloride (1:1); preliminary melting at 279° and final melting with decomposition at 283°–285°.

EXAMPLE 3

2-[2-[(4-Chlorophenyl)-3,6-dihydro-1(2H)-pyridinyl]ethyl]1H-benz[de]isoquinoline-1,3(2H)-dione, hydrochloride (1:1)

8.7 g. (0.022 mole) of the ester from Example 1(b) and 7.8 g. (0.040 mole) of 4-(p-chlorophenyl)-1,2,3,6-tetrahydropyridine (freed from the hydrochloride salt with aqueous NaOH and extracted into toluene) are refluxed in 250 ml. of toluene for 1 hour. The mixture is then cooled to 25° for 3 hours and the resulting precipitate filtered off. The filtrate is shaken with excess 10% HCl (aqueous) producing a precipitate that is insoluble in both layers. After several minutes the precipitate is filtered from the two liquid phases. Recrystallization of the filter cake by dissolving in 1 liter of hot 8:2 CHCl$_3$:EtOH, concentrating to 200 ml. and cooling, followed by drying at 80° (0.1 mm.) for 2 hours produces 5.6 g. of 2-[2-[(4-chlorophenyl)-3,6-dihydro-1(2H)-pyridinyl]ethyl]-1H-benz[de]isoquinoline-1,3(2H)-dione, hydrochloride (1:1); m.p. 287°–288° (dec.).

EXAMPLE 4

2-[2-[4-(Phenylmethyl)-1-piperidinyl]ethyl]-1H-benz-[de]isoquinoline-1,3(2H)-dione, hydrochloride (1:1)

10 g. (0.025 mole) of the ester from Example 1(b) and 9 g. (0.051 mole) of (4-phenylmethyl)piperidine are refluxed in 300 ml. of toluene for 1 hour, the solution becoming homogeneous at the reflux temperature. The mixture is then cooled to 25° for 3 hours and the resulting precipitate filtered off. The filtrate is washed with 10% NaOH then shaken with excess 10% HCl (aqueous) to produce a gum that is insoluble in both layers. After several minutes the gum crystallizes and is filtered from the two liquid phases. Recrystallization of the filter cake from 50% aqueous ethanol and drying at 85° (0.1 mm.) for 2 hours produces 7.2 g. of 2-[2-[4-(phenylmethyl)-1-piperidinyl]ethyl]-1H-benz-[de]isoquinoline-1,3-(2H)-dione, hydrochloride (1:1); m.p. 242°–244°.

EXAMPLE 5

2-[2-[4-(3-Phenylpropyl)-1-piperidinyl]ethyl]-1H-benz[de]isoquinoline-1,3(2H)-dione, hydrochloride (1:1)

10 g. (0.025 mole) of the ester from Example 1(b), 5.35 g. (0.026 mole) of 4-(3-phenylpropyl)piperidine and 3.26 g. (0.024 mole) of diisopropylethylamine are refluxed in 500 ml. of toluene for three hours. The reaction mixture is cooled, shaken with 10% KOH, washed with water (two washings, the aqueous layers are backwashed), and filtered. Shaking the toluene layer with the 10% HCl precipitates crude product which is then filtered from the two phases and washed with toluene and water. Recrystallization of the filter cake twice from absolute ethanol yields 7.0 g. of pure 2-[2-[4-(3-phenylpropyl)-1-piperidinyl]ethyl]-1H-benz[de]isoquinoline-1,3(2H)-dione, hydrochloride (1:1); m.p. 212°–213° (dec.).

EXAMPLE 6

2-[(3,6-Dihydro-4-phenyl-1(2H)-pyridinyl)methyl]-1H-benz[de]isoquinoline-1,3(2H)-dione 5 g. (0.025 mole) of 4-phenyl-1,2,3,6-tetrahydropyridine hydrochloride is dissolved in water, neutralized with 10% NaOH, and extracted into chloroform. The solvent is evaporated and the resulting free base added to 5 g. (0.025 mole) of 1,8-naphthalimide suspended in 20 ml. of DMF. 2.7 ml. of 37% aqueous formaldehyde (1 g., 0.03 mole) is added and the mixture heated at 100° until dissolution is complete. (ca. 5 min.). Then the solution is allowed to stand overnight at 25°. The resulting precipitate is filtered off, stirred in 100 ml. of acetonitrile, filtered off and dried at 60° (70 mm.) for 3 hours to yield 3.5 g. of 2-[(3,6-dihydro-4-phenyl-1(2H)-pyridinyl)methyl]-1H-benz[de]isoquinoline-1,3(2H)-dione; m.p. at 149°–152° (dec.).

EXAMPLE 7

2-[(4-Phenyl-1-piperidinyl)methyl]-1H-benz-[de]isoquinoline-1,3(2H)-dione

Following the procedure of Example 6 but substituting 4-phenylpiperidine for the 4-phenyl-1,2,3,6-tetrahydropyridine one obtains the 2-[(4-phenyl-1-piperidinyl)methyl]-1H-benz[de]isoquinoline-1,3(2H)-dione.

EXAMPLE 8

2-[3-(3,6-Dihydro-4-phenyl-1(2H)-pyridinyl)propyl]-1H-benz[de]isoquinoline-1,3(2H)-dione, hydrochloride (1:1)

a.

2-(3-Hydroxypropyl)-1H-benz[de]isoquinoline-1,3(2H)-dione, 4-methylbenzenesulfonate ester Following the procedure of Example 1(a) and (b) but substituting 3-aminopropanol for the ethanolamine in part (a) one obtains 2-(3-hydroxypropyl)-1H-benz[de]isoquinoline-1,3(2H)-dione, 4-methylbenzenesulfonate ester.

b.

2-[3-(3,6-Dihydro-4-phenyl-1(2H)-pyridinyl)propyl]-1H-benz[de]isoquinoline-1,3(2H)-dione, hydrochloride (1:1)

10.3 g. (0.025 mole) of the ester from part (a) and 8.1 g. (0.051 mole) of 4-phenyl-1,2,3,6-tetrahydropyridine (freed from the hydrochloride salt with aqueous NaOH, extracted into toluene and dried over 4A° molecular sieves) are refluxed in 300 ml. of toluene for 1 hour. The mixture is then cooled to 25° for 3 hours and the resulting precipitate filtered off. The filtrate is shaken with excess 10% HCl (aqueous) producing a gum that is insoluble in both layers. After several minutes the gum crystallizes and is filtered from the two liquid phases. Recrystallizations of the filter cake from 95% ethanol and drying at 80° (0.1 mm.) for 2 hours produces 3.5 g. of 2-[3-(3,6-dihydro-4-phenyl-1-(2H)-pyridinyl)propyl]-1H-benz[de]isoquinoline-1,3(2H)-dione, hydrochloride (1:1); which darkens at 242° and melts at 244°–245.5°.

EXAMPLE 9

2-[3-(4-phenyl-1-piperidinyl)propyl]-1H-benz-[de]isoquinoline-1,3-(2H)-dione, hydrochloride (1:1)

Following the procedure of Example 8 but substituting an equivalent amount of 4-phenylpiperidine for the 4-phenyl-1,2,3,6-tetrahydropyridine in part (b), one obtains 2-[3-(4-phenyl-1-piperidinyl)propyl]-1H-benz-[de]isoquinoline-1,3(2H)-dione, hydrochloride.

EXAMPLE 10

2-[4-(3,6-Dihydro-4-phenyl-1(2H)-pyridinyl)butyl]-1H-benz[de]isoquinoline-1,3(2H)-dione, hydrochloride (1:1)

a.

2-(4-Hydroxybutyl)-1H-benz[de]isoquinoline-1,3(2H)-dione, 4-methylbenzenesulfonate ester Following the procedure of Example 1(a) and (b) but substituting 4-aminobutanol for the ethanolamine in part (a) one obtains 2-(4-hydroxybutyl)-1H-benz-[de]isoquinoline-1,3(2H)-dione, 4-methylbenzenesulfonate ester.

b.

2-[4-(3,6-Dihydro-4-phenyl-1(2H)-pyridinyl)butyl]-1H-benz[de]isoquinoline-1,3(2H)-dione, hydrochloride (1:1)

10.6 g. (0.025 mole) of the ester from part (a) and 8.1 g. (0.051 mole) of 4-phenyl-1,2,3,6-tetrahydropyridine (freed from the hydrochloride salt with aqueous NaOH, extracted into chloroform and stripped of solvent) are refluxed in 300 ml. of toluene for 1 hour. The mixture is then cooled to 25° for 3 hours and the resulting precipitate filtered off. The filtrate is shaken with excess 10% HCl (aqueous), producing a gum that is insoluble in both layers. After several minutes, the gum crystallizes and is filtered from the two liquid phases. Recrystallization of the filter cake from ethanol-chloroform (2:1) and drying at 80° (0.1 mm.) for ten hours produces 9.8 g. of 2-[4-(3,6-dihydro-4-phenyl-1(2H)-pyridinyl)butyl]-1H-benz[de]isoquinoline-1,3(2H)-dione, hydrochloride (1:1); m.p. 250°–252°.

EXAMPLES 11–32

Following the procedure of Example 10 but substituting for the 4-phenyl-1,2,3,6-tetrahydropyridine an equivalent amount of one of the following:
4-phenylpiperidine
2-phenylpiperidine
3-phenylpiperidine
4-(2-phenylethyl)piperidine
4-(3-phenylpropyl)piperidine
4-(4-phenylbutyl)piperidine
3-(phenylmethyl)piperidine
2-(2-phenylethyl)piperidine
4-(4-chlorophenyl)piperidine
4-(4-fluorophenyl)piperidine
4-(3-trifluoromethylphenyl)piperidine
4-(3,4-dichlorophenyl)piperidine
4-(2-bromophenyl)piperidine
4-(3-methylphenyl)piperidine
4-(2-ethoxyphenyl)piperidine
4-(4-nitrophenyl)piperidine
3-(4-chlorophenyl)piperidine
2-(4-nitrophenyl)piperidine
4-[(4-chlorophenyl)methyl]piperidine
4-[2-(4-fluorophenyl)ethyl]piperidine
4-[3-(3-ethylphenyl)propyl]piperidine
3-[(2-bromophenyl)methyl]piperidine
one obtains:
2-[4-(4-phenyl-1-piperidinyl)butyl]-1H-benz-[de]isoquinoline-1,3(2H)-dione, hydrochloride (1:1);
2-[4-(2-phenyl-1-piperidinyl)butyl]-1H-benz-[de]isoquinoline-1,3(2H)-dione, hydrochloride (1:1);
2-[4-(3-phenyl-1-piperidinyl)butyl]-1H-benz-[de]isoquinoline-1,3(2H)-dione, hydrochloride (1:1);
2-[4-[4-(2-phenylethyl)-1-piperidinyl]butyl]-1H-benz[de]isoquinoline-1,3(2H)-dione, hydrochloride (1:1);
2-[4-[4-(3-phenylpropyl)-1-piperidinyl]butyl]-1H-benz[de]isoquinoline-1,3(2H)-dione, hydrochloride (1:1)
2-[4-[4-(4-phenylbutyl)-1-piperidinyl]butyl]-1H-benz[de]isoquinoline-1,3(2H)-dione, hydrochloride (1:1);
2-[4-(3-phenylmethyl-1-piperidinyl)butyl]-1H-benz-[de]isoquinoline-1,3(2H)-dione, hydrochloride (1:1);
2-[4-[2-(2-phenylethyl)-1-piperidinyl]butyl]-1H-benz[de]isoquinoline-1,3(2H)-dione, hydrochloride (1:1);
2-[4-[4-(4-chlorophenyl)-1-piperidinyl]butyl]-1H-benz[de]isoquinoline-1,3(2H)-dione, hydrochloride (1:1);
2-[4-[4-(4-fluorophenyl)-1-piperidinyl]butyl]-1H-benz[de]isoquinoline-1,3(2H)-dione, hydrochloride (1:1);
2-[4-[4-(3-trifluoromethylphenyl)-1-piperidinyl]butyl]-1H-benz[de]isoquinoline-1,3(2H)-dione, hydrochloride (1:1);
2-[4-[4-(3,4-dichlorophenyl)-1-piperidinyl]butyl]-1H-benz[de]isoquinoline-1,3(2H)-dione, hydrochloride (1:1);
2-[4-[4-(2-bromophenyl)-1-piperidinyl]butyl]-1H-benz[de]isoquinoline-1,3(2H)-dione, hydrochloride (1:1);
2-[4-[4-(3-methylphenyl)-1-piperidinyl]butyl]-1H-benz[de]isoquinoline-1,3(2H)-dione, hydrochloride (1:1);
2-[4-[4-(2-ethoxyphenyl)-1-piperidinyl]butyl]-1H-benz[de]isoquinoline-1,3(2H)-dione, hydrochloride (1:1);
2-[4-[4-(4-nitrophenyl)-1-piperidinyl]butyl]-1H-benz[de]isoquinoline-1,3(2H)-dione, hydrochloride (1:1);
2-[4-[3-(4-chlorophenyl)-1-piperidinyl]butyl]-1H-benz[de]isoquinoline-1,3(2H)-dione, hydrochloride (1:1);
2-[4-[2-(4-nitrophenyl)-1-piperidinyl]butyl]-1H-benz[de]isoquinoline-1,3(2H)-dione; hydrochloride (1:1);
2-[4-[4-[(4-chlorophenyl)methyl]-1-piperidinyl]butyl]-1H-benz[de]isoquinoline-1,3(2H)-dione, hydrochloride (1:1);
2-[4-[4-[2-(4-fluorophenyl)ethyl]-1-piperidinyl]butyl]-1H-benz[de]isoquinoline-1,3(2H)-dione, hydrochloride (1:1);
2-[4-[4-[3-(3-ethylphenyl)propyl]-1-piperidinyl]butyl]-1H-benz[de]isoquinoline-1,3(2H)-dione, hydrochloride (1:1); and 2-[4-[3-[(2-bromophenyl)methyl]-1-piperidinyl]-
butyl]-1H-benz[de]isoquinoline-1,3(2H)-dione,
hydrochloride (1:1); respectively.

Similarly, by employing the piperidine reactants of Examples 11 to 32 in the procedures of Examples 1, 7, or 9, other compounds within the scope of this invention are prepared.

EXAMPLES 33–55

Following the procedure of Example 10 but substituting for the 4-phenyl-1,2,3,6-tetrahydropyridine an equivalent amount of one of the following:

2-phenyl-1,2,3,6-tetrahydropyridine
3-phenyl-1,2,3,6-tetrahydropyridine
5-phenyl-1,2,3,6-tetrahydropyridine
6-phenyl-1,2,3,6-tetrahydropyridine
4-(phenylmethyl)-1,2,3,6-tetrahydropyridine
4-(2-phenylethyl)-1,2,3,6-tetrahydropyridine
4-(3-phenylpropyl)-1,2,3,6-tetrahydropyridine
4-(4-phenylbutyl)-1,2,3,6-tetrahydropyridine
3-(phenylmethyl)-1,2,3,6-tetrahydropyridine
4-(4-chlorophenyl)-1,2,3,6-tetrahydropyridine
4-(4-fluorophenyl)-1,2,3,6-tetrahydropyridine
4-(3-trifluoromethylphenyl)-1,2,3,6-tetrahydropyridine
4-(3,4-dichlorophenyl)-1,2,3,6-tetrahydropyridine
4-(2-bromophenyl)-1,2,3,6-tetrahydropyridine
4-(3-methylphenyl)-1,2,3,6-tetrahydropyridine
4-(2-ethoxyphenyl)-1,2,3,6-tetrahydropyridine
4-(4-nitrophenyl)-1,2,3,6-tetrahydropyridine
3-(4-chlorophenyl)-1,2,3,6-tetrahydropyridine
2-(4-nitrophenyl)-1,2,3,6-tetrahydropyridine
4-[(4-chlorophenyl)methyl]-1,2,3,6-tetrahydropyridine
4-[2-(4-fluorophenyl)ethyl]-1,2,3,6-tetrahydropyridine
4-[3-(3-ethylphenyl)propyl]-1,2,3,6-tetrahydropyridine
3-(2-bromophenyl)methyl-1,2,3,6-tetrahydropyridine one obtains 2-[4-(3,6-dihydro-2-phenyl-1(2H)-pyridinyl)butyl]-1H-benz[de]isoquinoline-1,3(2H)-dione, hydrochloride (1:1);
2-[4-(3,6-dihydro-3-phenyl-1(2H)-pyridinyl)butyl]-1H-benz[de]isoquinoline-1,3(2H)-dione, hydrochloride (1:1);
2-[4-(3,6-dihydro-5-phenyl-1(2H)-pyridinyl)butyl]-1H-benz[de]isoquinoline-1,3(2H)-dione, hydrochloride (1:1);
2-[4-(3,6-dihydro-6-phenyl-1(2H)-pyridinyl)butyl]-1H-benz[de]isoquinoline-1,3(2H)-dione, hydrochloride (1:1);
2-[4-[3,6-dihydro-4-(phenylmethyl)-1(2H)-pyridinyl]butyl]-1H-benz[de]isoquinoline-1,3(2H)-dione, hydrochloride (1:1);
2-[4-[3,6-dihydro-4-(2-phenylethyl)-1(2H)-pyridinyl]butyl]-1H-benz[de]isoquinoline-1,3(2H)-dione, hydrochloride (1:1);
2-[4-[3,6-dihydro-4-(3-phenylpropyl)-1(2H)-pyridinyl]butyl]-1H-benz[de]isoquinoline-1,3(2H)-dione, hydrochloride (1:1);
2-[4-[3,6-dihydro-4-(4-phenylbutyl)-1(2H)-pyridinyl]butyl]-1H-benz[de]isoquinoline-1,3(2H)-dione, hydrochloride (1:1);
2-[4-[3,6-dihydro-3-(phenylmethyl)-1(2H)-pyridinyl]butyl]-1H-benz[de]isoquinoline-1,3(2H)-dione, hydrochloride (1:1);
2-[4-[3,6-dihydro-4-(4-chlorophenyl)-1(2H)-pyridinyl]butyl]-1H-benz[de]isoquinoline-1,3(2H)-dione, hydrochloride (1:1);
2-[4-[3,6-dihydro-4-(4-fluorophenyl)-1(2H)-pyridinyl]butyl]-1H-benz[de]isoquinoline-1,3(2H)-dione, hydrochloride (1:1);
2-[4-[3,6-dihydro-4-(3-trifluoromethylphenyl)-1(2H)-pyridinyl]butyl]-1H-benz[de]isoquinoline-1,3(2H)-dione, hydrochloride (1:1);
2-[4-[3,6-dihydro-4-(3,4-dichlorophenyl)-1(2H)-pyridinyl]butyl]-1H-benz[de]isoquinoline-1,3(2H)-dione, hydrochloride (1:1);
2-[4-[3,6-dihydro-4-(2-bromophenyl)-1(2H)-pyridinyl]butyl]-1H-benz[de]isoquinoline-1,3(2H)-dione, hydrochloride (1:1);
2-[4-[3,6-dihydro-4-(3-methylphenyl)-1(2H)-pyridinyl]butyl]-1H-benz[de]isoquinoline-1,3(2H)-dione, hydrochloride (1:1);
2-[4-[3,6-dihydro-4-(2-ethoxyphenyl)-1(2H)-pyridinyl]butyl]-1H-benz[de]isoquinoline-1,3(2H)-dione, hydrochloride (1:1);
2-[4-[3,6-dihydro-4-(4-nitrophenyl)-1(2H)-pyridinyl]butyl]-1H-benz[de]isoquinoline-1,3(2H)-dione, hydrochloride (1:1);
2-[4-[3,6-dihydro-3-(4-chlorophenyl)1(2H)-pyridinyl]butyl]-1H-benz[de]isoquinoline-1,3(2H)-dione, hydrochloride (1:1);
2-[4-[3,6-dihydro-2-(4-nitrophenyl)-1(2H)-pyridinyl]butyl]-1H-benz[de]isoquinoline-1,3(2H)-dione, hydrochloride (1:1);
2-[4-[3,6-dihydro-4-[(4-chlorophenyl)methyl]-1(2H)-pyridinyl]butyl]-1H-benz[de]isoquinoline-1,3(2H)-dione, hydrochloride (1:1);
2-[4-[3,6-dihydro-4-[2-(4-fluorophenyl)ethyl]-1(2H)-pyridinyl]butyl]-1H-benz[de]isoquinoline-1,3(2H)-dione, hydrochloride (1:1);
2-[4-[3,6-dihydro-4-[3-(3-ethylphenyl)propyl]-1(2H)-pyridinyl]butyl]-1H-benz[de]isoquinoline-1,3(2H)-dione, hydrochloride (1:1); and
2-[4-[3,6-dihydro-3-[(2-bromophenyl)methyl]-1(2H)-pyridinyl]butyl]-1H-benz[de]isoquinoline-1,3(2H)-dione, hydrochloride (1:1); respectively.

Similarly, by employing the tetrahydropyridine reactants of Examples 33 to 55 in the procedures of Examples 2, 6, or 8, other compounds within the scope of this invention are prepared.

EXAMPLE 56

2-[6-(3,6-Dihydro-4-phenyl-1(2H)-pyridinyl)hexyl]-1H-benz[de]isoquinoline-1,3(2H)-dione, hydrochloride (1:1)

a.

2-(6-Bromohexyl)-1H-benz[de]isoquinoline-1,3(2H)-dione 100 g. (0.5 mole) of 1,8-naphthalimide are suspended in 2100 ml. of dimethylformamide and the mixture is heated to 90° to form a complete solution. A solution of 36.3 g. (0.55 mole) of potassium hydroxide (85%) in 100 ml. of methanol is added resulting in the immediate formation of a yellow precipitate. The resulting mixture is stirred for one hour at 90° and cooled to 25°. 245 g. (1.0 mole) of 1,6-dibromohexane are added and the mixture is again heated to 90° and stirred for an additional hour. A precipitate remains in the mixture but is more granular than the initial material. The reaction mixture is cooled and the precipitate filtered off. The solvent is removed under vacuum and the residue is diluted with 500 ml. of hexane immediately precipitating crude 2-(6-bromohexyl)-1H-benz-[de]isoquinoline-1,3(2H)-dione. The precipitate is filtered off, washed with fresh hexane and dried for 2 hours at 50° ( 0.1 mm.) to yield 148 g. of 2-(6-bromohexyl)-1H-benz[de]isoquinoline-1,3(2H)-dione. An analytically pure sample is prepared by dissolving the above product in hot 95% ethanol and recrystallizing by allowing the solution to cool to 25°. The resulting precipitate is dried for two hours at 50° (0.1 mm.) to yield pure 2-(6-bromohexyl)-1H-benz[de]isoquinoline-1,3(2H)-dione, m.p. 95°–96°.

b.
2-[6-(3,6-Dihydro-4-phenyl-1(2H)-pyridinyl)hexyl]-1H-benz[de]isoquinoline-1,3(2H)-dione, hydrochloride (1:1)

18 g. (0.05 mole) of 2-(6-bromohexyl)-1H-benz-[de]isoquinoline-1,3(2H)-dione, from part (a), 8.8 g. (0.055 mole) of 4-phenyl-1,2,3,6-tetrahydropyridine (obtained from hydrochloride salt), and 6.5 g. (0.05 mole) of diisopropylethylamine are refluxed in 500 ml. of toluene for 4 hours. The reaction mixture is washed with 10% potassium hydroxide and the toluene solution is then filtered through sintered glass. The filtrate is shaken with excess 10% HCl forming a precipitate. The precipitate is filtered from the two liquid phases and recrystallized from hot 95% ethanol which contains sufficient $CHCl_3$ to get all of the material into the hot solution. The resulting precipitate is dried for 2 hours at 50° (0.1 mm.) to yield 9.0 g. of 2-[6-(3,6-dihydro-4-phenyl-1(2H)-pyridinyl)hexyl]-1H-benz[de]isoquinoline-1,3(2H)-dione, hydrochloride (1:1); m.p. 259°–261°.

The free base when isolated from the above salt has a m.p. of 107°–109°.

EXAMPLE 57

2-[6-(4-Phenyl-1-piperidinyl)hexyl]-1H-benz-[de]isoquinoline-1,3(2H)-dione, hydrochloride (1:1)

Following the procedure of Example 56 but substituting 4-phenylpiperidine for the 4-phenyl-1,2,3,6-tetrahydropyridine in part (b), one obtains 2-[6-(4-phenyl-1-piperidinyl)hexyl]-1H-benz[de]isoquinoline-1,3(2H)-dione, hydrochloride (1:1).

EXAMPLE 58

2-[5-(3,6-Dihydro-4-phenyl-1(2H)-pyridinyl)pentyl]-1H-benz[de]isoquinoline-1,3(2H)-dione, hydrochloride (1:1)

a.
2-(5-Bromopentyl)-1H-benz[de]isoquinoline-1,3(2H)-dione

Following the procedure of part (a) of Example 56 but substituting 1,5-dibromopentane for the 1,6-dibromohexane, one obtains 2-(5-bromopentyl)-1H-benz[de]isoquinoline-1,3(2H)-dione; m.p. 113°–115°.

b.
2-[5-(3,6-Dihydro-4-phenyl-1(2H)-pyridinyl)pentyl]-1H-benz[de]isoquinoline-1,3(2H)-dione, hydrochloride (1:1)

Following the procedure of part (b) of Example 56 but substituting 2-(5-bromopentyl)-1H-benz[de]isoquinoline-1,3(2H)-dione for the 2-(6-bromohexyl)-1H-benz[de]isoquinoline-1,3(2H)-dione, one obtains 2-[5-(3,6-dihydro-4-phenyl-1(2H)-pyridinyl)pentyl]-1H-benz[de]isoquinoline-1,3(2H)-dione, hydrochloride (1:1). The product is purified by recrystallization from n-butanol; m.p. 207°–210°.

Similarly, by employing the tetrahydropyridine reactants of Examples 33 to 55 in the procedures of Example 56 or 58, other compounds within the scope of this invention are prepared.

EXAMPLE 59

2-[5-(4-Phenyl-1-piperidinyl)pentyl]-1H-benz-[de]isoquinoline-1,3(2H)-dione, hydrochloride (1:1)

Following the procedure of Example 58 but substituting 4-phenylpiperidine for the 4-phenyl-1,2,3,6-tetrahydropyridine in part (b), one obtains 2-[5-(4-phenyl)-1-piperidinyl)pentyl]-1H-benz[de]isoquinoline-1,3(2H)-dione, hydrochloride (1:1).

Similarly, by employing the piperidine reactants of Examples 11 to 32 in the procedures of Examples 57 or 59, other compounds within the scope of this invention are prepared.

EXAMPLES 60–68

Following the procedure of Example 2 but substituting the alkanolamine shown in Col. I for the ethanolamine the following products are obtained wherein A is the radical shown in Col. II.

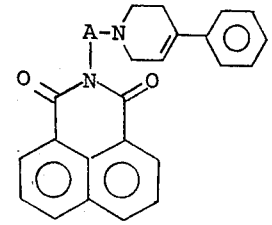

| Ex. | Col. I | Col. II |
|---|---|---|
| 60 | $H_2N—(CH_2)_5—OH$ | $—(CH_2)_5—$ |
| 61 | $H_2N—(CH_2)_6—OH$ | $—(CH_2)_6—$ |
| 62 | $H_2N—(CH_2)_7—OH$ | $—(CH_2)_7—$ |
| 63 | $H_2N—(CH_2)_8—OH$ | $—(CH_2)_8—$ |
| 64 | $H_2N—CH_2—\underset{\underset{CH_3}{\mid}}{CH}—CH_2—OH$ | $—CH_2—\underset{\underset{CH_3}{\mid}}{CH}—CH_2—$ |
| 65 | $H_2N—\underset{\underset{CH_3}{\mid}}{CH}—(CH_2)_3—OH$ | $—\underset{\underset{CH_3}{\mid}}{CH}—(CH_2)_3—$ |
| 66 | $H_2N—(CH_2)_3—\underset{\underset{CH_3}{\mid}}{CH}—OH$ | $—(CH_2)_3—\underset{\underset{CH_3}{\mid}}{CH}—$ |
| 67 | $H_2N—CH_2—\underset{\underset{C_3H_7}{\mid}}{CH}—(CH_2)_2—OH$ | $—CH_2—\underset{\underset{C_3H_7}{\mid}}{CH}—(CH_2)_2—$ |
| 68 | $H_2N—\underset{\underset{CH_3}{\mid}}{CH}—CH_2—\underset{\underset{CH_3}{\mid}}{CH}—OH$ | $—\underset{\underset{CH_3}{\mid}}{CH}—CH_2—\underset{\underset{CH_3}{\mid}}{CH}—$ |

Similarly, by employing the alkanolamines of Examples 60 to 68 in the procedures of Examples 1, 3 to 5 or 8 to 55, other compounds within the scope of this invention are prepared.

Alternatively, the procedures of Examples 56 to 59 can be employed to prepare the products of Examples 1 to 5, 8 to 55, and 62 to 68.

EXAMPLE 69

5-Chloro-2-[2-(3,6-dihydro-4-phenyl-1(2H)-pyridinyl)ethyl]-1H-benz[de]isoquinoline-1,3(2H)-dione, hydrochloride (1:1)

a.

5-Chloro-2-(2-hydroxyethyl)-1H-benz[de]isoquinoline-1,3(2H)-dione, 4-methylbenzenesulfonate ester Following the procedure of Example 1(a) and (b) but substituting 3-chloronaphthalic anhydride for the naphthalic anhydride one obtains 5-chloro-2-(2-hydroxyethyl)-1H-benz[de]isoquinoline-1,3(2H)-dione, 4-methylbenzenesulfonate ester.

300 ml., adding 300 ml. of hot abs. ethanol cooling and filtering off the resulting precipitate. Drying at 90° (0.1 mm.) for 3 hours yields 2.8 g. of 5-chloro-2-[2-(3,6-dihydro-4-phenyl-1(2H)-pyridinyl)ethyl]-1H-benz[de]isoquinoline-1,3(2H)-dione, hydrochloride (1:1); m.p. 273°–275° (dec.).

EXAMPLES 70–95

Following the procedure of Example 10 but substituting for the 2-(4-hydroxybutyl)-1H-benz[de]isoquinoline-1,3(2H)-dione, 4-methylbenzenesulfonate ester the ester shown in Col. I one obtains the product shown in Col. II.

Col. I

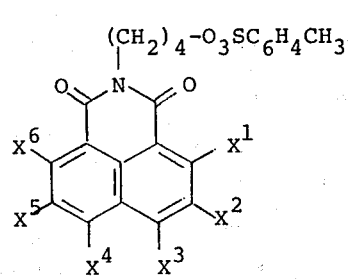

Col. II

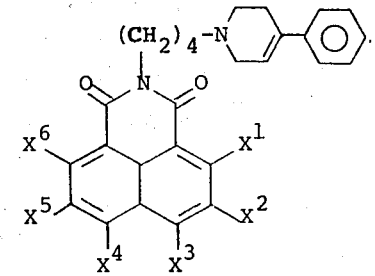

| Ex. | X¹ | X² | X³ | X⁴ | X⁵ | X⁶ |
|-----|----|----|----|----|----|----|
| 70 | H | H | Cl | H | H | H |
| 71 | H | Cl | H | H | H | H |
| 72 | H | Br | H | H | H | H |
| 73 | H | F | H | H | H | H |
| 74 | H | I | H | H | H | H |
| 75 | H | Cl | H | H | Cl | H |
| 76 | Br | H | H | H | H | H |
| 77 | H | H | Cl | Cl | H | H |
| 78 | H | H | CH₃ | H | H | H |
| 79 | H | H | C₂H₅ | H | H | H |
| 80 | H | H | i-C₃H₇ | H | H | H |
| 81 | H | H | CH₃ | CH₃ | H | H |
| 82 | H | H | OCH₃ | H | H | H |
| 83 | H | H | OC₂H₅ | H | H | H |
| 84 | H | H | OC₃H₇ | H | H | H |
| 85 | H | H | OCH₃ | OCH₃ | H | H |
| 86 | H | NO₂ | H | H | H | H |
| 87 | H | H | NO₂ | H | H | H |
| 88 | H | CF₃ | H | H | H | H |
| 89 | H | H | CF₃ | H | H | H |
| 90 | H | CN | H | H | H | H |
| 91 | H | H | CN | H | H | H |
| 92 | H | H | NH₂ | H | H | H |
| 93 | H | NH₂ | H | H | H | H |
| 94 | H | SC₂H₅ | H | H | H | H |
| 95 | H | H | SCH₃ | H | H | H | b.

5-Chloro-2-[2-(3,6-dihydro-4-phenyl-1(2H)-pyridinyl)ethyl]-1H-benz[de]isoquinoline-1,3(2H)-dione, hydrochloride (1:1)

10 g. (0.0234 mole) of the ester from part (a) and 7.5 g. (0.047 mole) of 4-phenyl-1,2,3,6-tetrahydropyridine (freed from the salt with aqueous NaOH, extracted into toluene and dried over 4A° molecular sieves) are refluxed in 300 ml. of toluene for 3 hours. The mixture is then cooled to 25° for 1 hour and the resulting precipitate filtered off. The filtrate is shaken with excess 10% HCl (aqueous) producing a gum that is insoluble in both layers. After several minutes the gum crystallizes and is filtered from the two liquid phases. Recrystallization of the filter cake is accomplished by dissolving the salt in 1000 ml. of hot chloroform, evaporating down to Similarly, by employing the ester of Col. I of Examples 70–95 in the procedures of Examples 1–5, 8, 9, 11–55 and 60–69, other compounds within the scope of this invention are prepared. Similarly, by following the procedures of Examples 6 and 7 but employing a substituted 1,8-naphthalimide of formula VII wherein the substituents are those listed under the headings X¹, X², X³, X⁴, X⁵, and X⁶ in Examples 70 to 95, other compounds within the scope of this invention are prepared.

EXAMPLE 96

2-[2-(4-Hydroxy-4-phenyl-1-piperidinyl)ethyl]-1H-benz[de]isoquinoline-1,3(2H)-dione 10 g. (0.025 mole) of the ester from Example 1(b), 4.9 g. (0.028 mole) of (4-hydroxy-4-phenyl)piperidine, and 3.26 g. (0.025 mole) of diisopropylethylamine in 200 ml. of toluene are refluxed for 3.5 hours. The toluene is evaporated and the residue is taken up in chloroform, washed with 10% KOH, filtered, and washed with water (all aqueous layers are backwashed). The chloroform layers are combined and warmed with activated carbon, filtered, and evaporated. The residue is recrystallized from ethanol and toluene to yield 2.2 g. of 2-[2-(4-hydroxy-4-phenyl-1-piperidinyl)ethyl]-1H-benz[de]isoquinoline-1,3(2H)-dione; m.p. 177°–179°.

EXAMPLES 97–100

Following the procedure of Example 96 but substituting for the 2-(2-hydroxyethyl-1H-benz[de]isoquinoline-1,3(2H)-dione, 4-methylbenzenesulfonate ester one of the following:

2-(3-hydroxypropyl)-1H-benz[de]isoquinoline-
1,3(2H)-dione, 4-methylbenzenesulfonate ester;

2-(4-hydroxybutyl)-1H-benz[de]isoquinoline-
1,3(2H)-dione, 4-methylbenzenesulfonate ester;

2-(5-hydroxypentyl)-1H-benz[de]isoquinoline-
1,3(2H)-dione, 4-methylbenzenesulfonate ester;

2-(6-hydroxyhexyl)-1H-benz[de]isoquinoline-
1,3(2H)-dione, 4-methylbenzenesulfonate ester;
one obtains:

2-[3-(4-hydroxy-4-phenyl-1-piperidinyl)propyl]-1H-
benz[de]isoquinoline-1,3(2H)-dione;

2-[4-(4-hydroxy-4-phenyl-1-piperidinyl)butyl]-1H-
benz[de]isoquinoline-1,3(2H)-dione;

2-[5-(4-hydroxy-4-phenyl-1-piperidinyl)pentyl]-1H-
benz[de]isoquinoline-1,3(2H)-dione; and 2-[6-(4-hydroxy-4-phenyl-1-piperidinyl)hexyl]-1H-
benz[de]isoquinoline-1,3(2H)-dione; respectively.

Similarly, by employing the alkanolamines of Examples 62 to 68 or the substituted esters of Examples 70 to 95, other compounds within the scope of the invention are obtained.

EXAMPLES 101–117

Following the procedure of Example 98 but substituting for the (4-hydroxy-4-phenyl)piperidine one of the following:

(3-hydroxy-3-phenyl)piperidine
[4-hydroxy-4-(4-chlorophenyl)]piperidine
[4-hydroxy-4-(3-trifluoromethylphenyl)]piperidine
[4-hydroxy-4-(3-ethylphenyl)]piperidine
[4-hydroxy-4-(2-methoxyphenyl)]piperidine
[3-hydroxy-3-(4-bromophenyl)]piperidine
[4-hydroxy-4-(3,4-dichlorophenyl)]piperidine
[4-hydroxy-4-(4-nitrophenyl)]piperidine
[4-hydroxy-4-(phenylmethyl)]piperidine
[4-hydroxy-4-(2-phenylethyl)]piperidine
[4-hydroxy-4-(3-phenylpropyl)]piperidine
[3-hydroxy-3-[(4-chlorophenyl)methyl]]piperidine
[4-hydroxy-4-[(3-methoxyphenyl)methyl]]piperidine
[4-hydroxy-4-[(4-nitrophenyl)methyl]]piperidine
[4-hydroxy-4-[(3,4-dichlorophenyl)methyl]]piperidine
[4-hydroxy-4-[2-(4-fluorophenyl)ethyl]]piperidine
[4-hydroxy-4-[3-(4-methylphenyl)propyl]]piperidine
one obtains 2-[4-(3-hydroxy-3-phenyl-1-piperidinyl)butyl]-1H-
benz[de]isoquinoline-1,3(2H)-dione;

2-[4-[4-hydroxy-4-(4-chlorophenyl)-1-piperidinyl]-
butyl]-1H-benz[de]isoquinoline-1,3(2H)-dione;

2-[4-[4-hydroxy-4-(3-trifluoromethylphenyl)-1-
piperidinyl]butyl]-1H-benz[de]isoquinoline-
1,3(2H)-dione;

2-[4-[4-hydroxy-4-(3-ethylphenyl)-1-piperidinyl]-
butyl]-1H-benz[de]isoquinoline-1,3(2H)-dione;

2-[4-[4-hydroxy-4-(2-methoxyphenyl)-1-
piperidinyl]butyl]-1H-benz[de]isoquinoline-
1,3(2H)-dione;

2-[4-[3-hydroxy-3-(4-bromophenyl)-1-piperidinyl]-
butyl]-1H-benz[de]isoquinoline-1,3(2H)-dione;

2-[4-[4-hydroxy-4-(3,4-dichlorophenyl)-1-
piperidinyl]butyl]-1H-benz[de]isoquinoline-
1,3(2H)-dione;

2-[4-[4-hydroxy-4-(4-nitrophenyl)-1-piperidinyl]-
butyl]-1H-benz[de]isoquinoline-1,3(2H)-dione;

2-[4-[4-hydroxy-4-(phenylmethyl)-1-piperidinyl]-
butyl]-1H-benz[de]isoquinoline-1,3(2H)-dione;

2-[4-[4-hydroxy-4-(2-phenylethyl)-1-piperidinyl]-
butyl]-1H-benz[de]isoquinoline-1,3(2H)-dione;

2-[4-[4-hydroxy-4-(3-phenylpropyl)-1-piperidinyl]-
butyl]-1H-benz[de]isoquinoline-1,3(2H)-dione;

2-[4-[3-hydroxy13-[(4-chlorophenyl)methyl]-1-
piperidinyl]butyl]-1H-benz[de]isoquinoline-
1,3(2H)-dione;

2-[4-[4-hydroxy-4-[(3-methoxyphenyl)methyl]-1-
piperidinyl]butyl]-1H-benz[de]isoquinoline-
1,3(2H)-dione;

2-[4-[4-hydroxy-4-[(4-nitrophenyl)methyl]-1-
piperidinyl]butyl]-1H-benz[de]isoquinoline-
1,3(2H)-dione;

2-[4-[4-hydroxy-4-[(3,4-dichlorophenyl)methyl]-1-
piperidinyl]butyl]-1H-benz[de]isoquinoline-
1,3(2H)-dione;

2-[4-[4-hydroxy-4-[2-(4-fluorophenyl)ethyl]-1-
piperidinyl]butyl]-1H-benz[de]isoquinoline-
1,3(2H)-dione; and 2-[4-[4-hydroxy-4-[3-(4-methylphenyl)propyl]-1-
piperidinyl]butyl]-1H-benz[de]isoquinoline-
1,3(2H)-dione
respectively.

Similarly, by employing these disubstituted piperidines in the procedures of Examples 96, 97 and 99–100, other compounds within the scope of the invention are prepared.

What is claimed is:

1. A compound of the formula

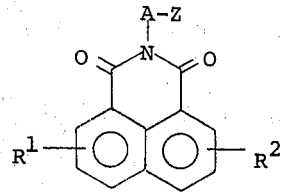

wherein $R^1$ and $R^2$ are each independently selected from the group consisting of hydrogen, chlorine, bromine, fluorine, straight or branched chain alkyl of 1 to 4 carbons, straight or branched chain alkoxy of 1 to 4 carbons, straight or branched chain alkylthio of 1 to 4 carbons, nitro, amino, cyano and trifluoromethyl; A is a straight or branched chain alkylene of 1 to 8 carbons; and Z is selected from the group consisting of

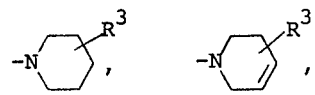

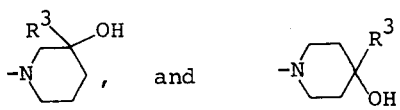

wherein R³ is selected from the group consisting of phenyl, phenyl-alkyl, substituted phenyl and phenyl-alkyl wherein said alkyl is straight or branched chain of 1 to 4 carbons and said phenyl substituent is selected from the group consisting of chlorine, bromine, fluorine, di(chloro), di(bromo), straight or branched chain alkyl of 1 to 4 carbons, di(methyl), straight or branched chain alkoxy of 1 to 4 carbons, nitro, amino, and trifluoromethyl; and the pharmaceutically acceptable acid addition salts thereof.

2. The compound of claim 1 wherein at least one of R¹ and R² is hydrogen and the other is selected from the group consisting of hydrogen, Cl, Br, F, methyl and methoxy; and A is a straight or branched chain alkylene of 1 to 6 carbons.

3. The compound of claim 2 wherein R¹ and R² are both hydrogen; A is a straight chain alkylene of 2 to 6 carbons; and Z is selected from the group consisting of

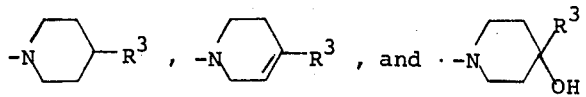

4. The compound of claim 3 wherein Z is

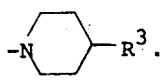

5. The compound of claim 4 having the name 2-[2-(4-phenyl-1-piperidinyl)ethyl]-1H-benz[de]isoquinoline-1,3(2H)-dione, hydrochloride (1:1).

6. The compound of claim 4 having the name 2-[2-[4-(phenylmethyl)-1-piperidinyl]ethyl]-1H-benz[de]isoquinoline-1,3(2H)-dione, hydrochoride (1:1).

7. The compound of claim 4 having the name 2-[2-[4-(3-phenylpropyl)-1-piperidinyl]ethyl]-1H-benz[de]isoquinoline-1,3(2H)-dione, hydrochloride (1:1).

8. The compound of claim 4 having the name 2-[3-(4-phenyl-1-piperidinyl)propyl]-1H-benz[de]isoquinoline-1,3(2H)-dione, hydrochloride (1:1).

9. The compound of claim 4 having the name 2-[4-(4-phenyl-1-piperidinyl)butyl]-1H-benz[de]isoquinoline-1,3(2H)-dione, hydrochloride (1:1).

10. The compound of claim 4 having the name 2-[5-(4-phenyl-1-piperidinyl)pentyl]-1H-benz[de]isoquinoline-1,3(2H)-dione, hydrochloride (1:1).

11. The compound of claim 4 having the name 2-[6-(4-phenyl-1-piperidinyl)hexyl]-1H-benz[de]isoquinoline-1,3(2H)-dione, hydrochloride (1:1).

12. The compound of claim 3 wherein Z is

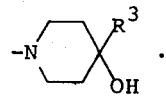

13. The compound of claim 12 having the name 2-[2-(4-hydroxy-4-phenyl-1-piperidinyl)ethyl]-1H-benz[de]isoquinoline-1,3(2H)-dione.

14. The compound of claim 12 having the name 2-[3-(4-hydroxy-4-phenyl-1-piperidinyl)propyl]-1H-benz[de]isoquinoline-1,3(2H)-dione.

15. The compound of claim 12 having the name 2-[4-(4-hydroxy-4-phenyl-1-piperidinyl)butyl]-1H-benz[de]isoquinoline-1,3(2H)-dione.

16. The compound of claim 3 where Z is

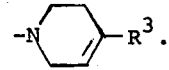

17. The compound of claim 16 having the name 2-[2-(3,6-dihydro-4-phenyl-1(2H)-pyridinyl)ethyl]-1H-benz[de]isoquinoline-1,3(2H)-dione, hydrochloride (1:1).

18. The compound of claim 16 having the name 2-[2-[(4-chlorophenyl)-3,6-dihydro-1(2H)-pyridinyl]ethyl]-1H-benz[de]isoquinoline-1,3(2H)-dione, hydrochloride (1:1).

19. The compound of claim 16 having the name 2-[3-(3,6-dihydro-4-phenyl-1(2H)-pyridinyl)propyl]-1H-benz[de]isoquinoline-1,3(2H)-dione, hydrochloride (1:1).

20. The compound of claim 16 having the name 2-[4-(3,6-dihydro-4-phenyl-1(2H)-pyridinyl)butyl]-1H-benz[de]isoquinoline-1,3(2H)-dione, hydrochloride (1:1).

21. The compound of claim 16 having the name 2-[5-(3,6-dihydro-4-phenyl-1(2H)-pyridinyl)pentyl]-1H-benz[de]isoquinoline-1,3(2H)-dione, hydrochloride (1:1).

22. The compound of claim 16 having the name 2-[6-(3,6-dihydro-4-phenyl-1(2H)-pyridinyl)hexyl]-1H-benz[de]isoquinoline-1,3(2H)-dione, hydrochloride (1:1).

23. The compound of claim 2 having the name 2-[(4-phenyl-1-piperidinyl)methyl]-1H-benz[de]isoquinoline-1,3(2H)-dione.

24. The compound of claim 2 having the name 2-[(3,6-dihydro-4-phenyl-1(2H)-pyridinyl)methyl]-1H-benz[de]isoquinoline-1,3(2H)-dione.

25. The compound of claim 2 having the name 5-chloro-2-[2-(3,6-dihydro-4-phenyl-1(2H)-pyridinyl)ethyl]-1H-benz[de]isoquinoline-1,3(2H)-dione, hydrochloride (1:1).

* * * * *